United States Patent [19]

Doring

[11] 4,301,815
[45] Nov. 24, 1981

[54] TRAILING TINE ELECTRODE LEAD

[75] Inventor: Carl Doring, Wollstonecraft, Australia

[73] Assignee: Telectronics Pty. Limited, Lane Cove, Australia

[21] Appl. No.: 114,950

[22] Filed: Jan. 23, 1980

[51] Int. Cl.³ .............................................. A61N 1/04
[52] U.S. Cl. .............................. 128/785; 128/419 P; 128/786
[58] Field of Search ...................... 128/419 P, 784–786

[56] References Cited

U.S. PATENT DOCUMENTS

| | | | |
|---|---|---|---|
| 2,854,983 | 10/1958 | Baskin | 128/349 |
| 3,348,548 | 10/1967 | Chardack | 128/419 P |
| 3,397,699 | 8/1968 | Kohl | 128/349 |
| 3,516,410 | 6/1970 | Hakim | 128/350 |
| 3,568,659 | 3/1971 | Karnegis | 128/1 R |
| 3,608,555 | 9/1971 | Greyson | 128/348 |
| 3,717,151 | 2/1973 | Collett | 128/347 |
| 3,719,190 | 3/1973 | Avery | 128/419 P |
| 3,754,555 | 8/1973 | Schmitt | 128/419 P |
| 3,815,608 | 6/1974 | Spinosa | 128/349 R |
| 3,835,864 | 9/1974 | Rasor et al. | 128/419 P |
| 3,939,843 | 2/1976 | Smyth | 128/419 P |
| 3,976,082 | 8/1976 | Schmitt | 128/419 P |
| 4,030,508 | 6/1977 | Thalen | 128/419 P |
| 4,033,357 | 7/1977 | Helland et al. | 128/419 P |

FOREIGN PATENT DOCUMENTS

| | | | |
|---|---|---|---|
| 490702 | 1/1975 | Australia. | |
| 482097 | 7/1976 | Australia. | |
| 5106 | 10/1979 | European Pat. Off. | 128/419 P |
| 2133304 | 1/1973 | Fed. Rep. of Germany. | |
| 2302107 | 2/1975 | France. | |
| 1371033 | 9/1970 | United Kingdom | 128/419 P |
| 1546107 | 8/1975 | United Kingdom | 128/419 P |
| 1576587 | 3/1977 | United Kingdom | 128/419 P |
| 1482281 | 8/1977 | United Kingdom | 128/419 P |
| 1491942 | 11/1977 | United Kingdom | 128/419 P |
| 1495162 | 12/1977 | United Kingdom | 128/419 P |
| 1537101 | 12/1978 | United Kingdom | 128/419 P |

OTHER PUBLICATIONS

Medtronic Literature—Appendices A, B, I, N–O & Q–R, No other Bibliographic Data available.
Pellegrini, "Pacemaker Colloquium", Arnhem (Vitatron), 1975—No other Bibliographic Data available.
Pieper, "Review of Scientific Instruments, vol. 29, No. 11, Nov. 1958, pp. 965–967.
Wenpe et al., "Deutsche Medizinische Wochewschrift", J. 95, Nr. 40, 2 Oct. 1970, Z.2026–2028.
Schaldach, "Transactions for the American Society for Artificial Internal Organs, vol. 17, 1971, pp. 29–35.

*Primary Examiner*—William E. Kamm
*Attorney, Agent, or Firm*—Finnegan, Henderson, Farabow, Garrett & Dunner

[57] ABSTRACT

A medically implantable electrode lead for muscle stimulation comprising an electrode assembly with an exposed conductive distal tip which is coupled by an electrical conductor to a source of electrical pulses. The electrode assembly and electrical conductor are encased in an electrical insulator. The insulator has extending from it a plurality of flexible tines which are adapted to hold the exposed distal tip into position. To facilitate insertion of the distal tip into the desired location, especially when inserting the distal tip through a small opening such as a small vein, the insulator includes a transitional, truncated cone section between the distal tip and the tines. The outside diameter of the distal end of the cone section equals the outside diameter of the distal tip and the outside diameter of the proximal end of the cone section equals the outside diameter of the tines when they are folded into a closed position.

20 Claims, 18 Drawing Figures

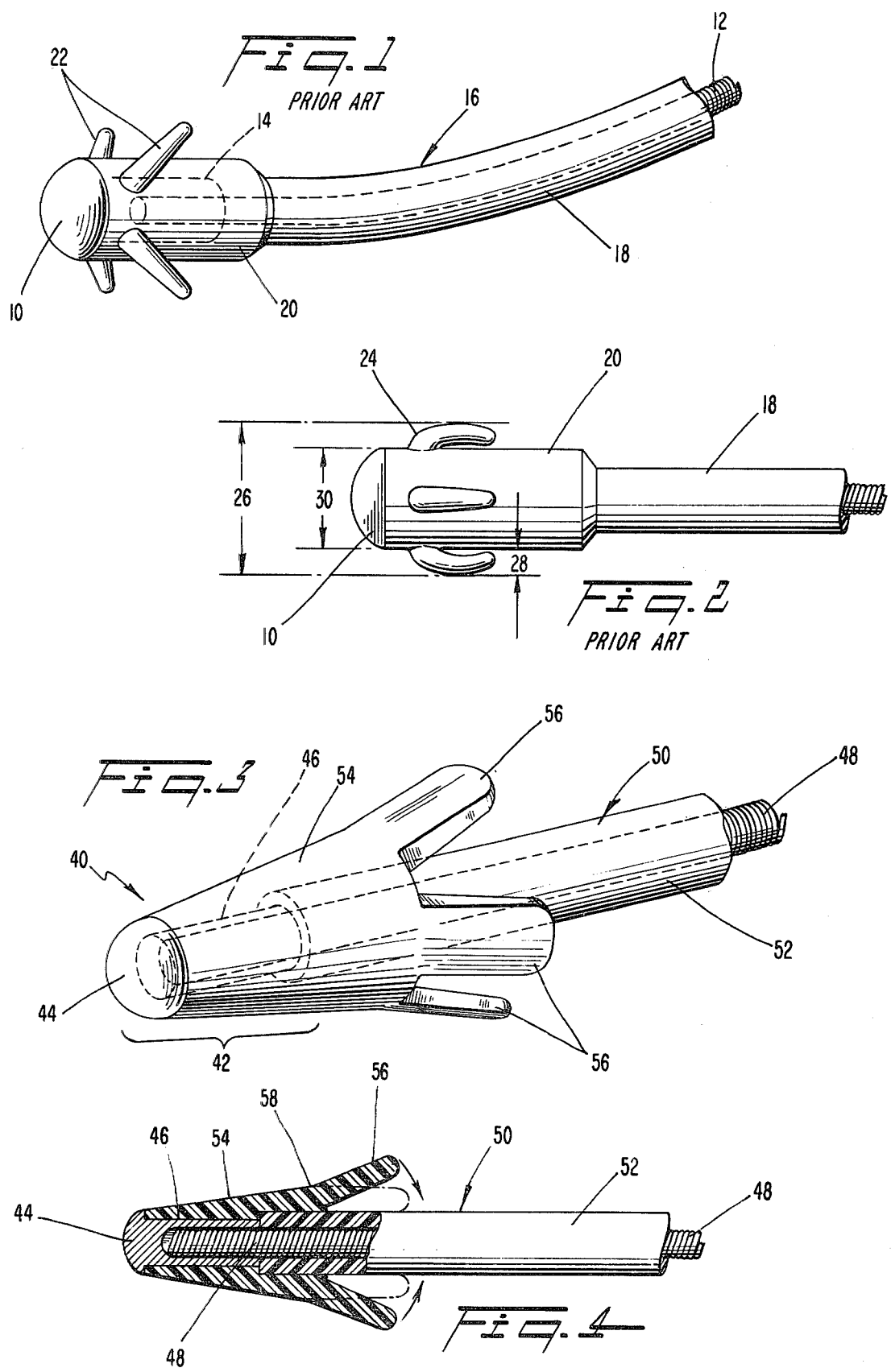

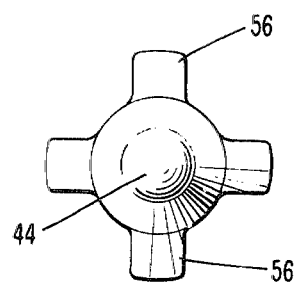
Fig.5
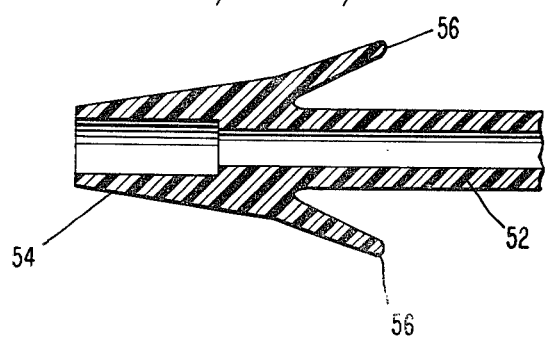
Fig.6
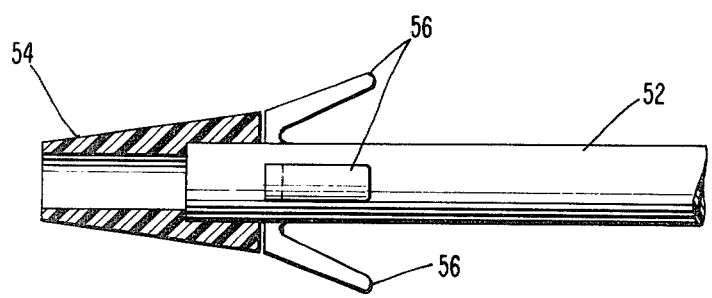
Fig.7
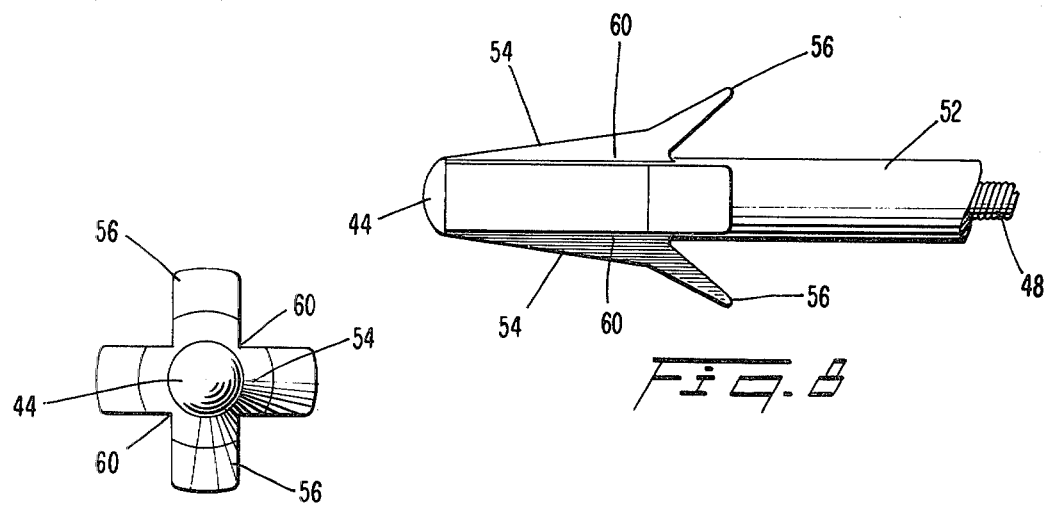
Fig.8
Fig.9

TRAILING TINE ELECTRODE LEAD

BACKGROUND OF THE INVENTION

The present invention relates to a medical electrode lead employing flexible tines to hold the distal tip of the electrode in place.

Today there are available many forms of medical electrode leads which are provided with a metallic distal tip which is placed adjacent to excitable tissue, such as the inside wall of the heart. Electric current supplied to the distal tip stimulates the muscle in contact with the tip.

There are three apparently conflicting demands placed upon the geometric configuration of such medical electrode leads. First, it is vitally important that the electrode lead have an effective anchoring configuration so that once the distal tip is correctly positioned it remains in that position. Second, the electrode lead must also be small enough and have a sufficiently smooth surface to allow for passage through tight places, such as the inside of small blood vessels, in order to reach the desired location. Third, the electrode lead must be capable of being removed from an anchored position, especially during the process of initially positioning the distal tip.

The prior art devices evidence many and varying attempts to solve these conflicts. Some employ a truncated cone section behind the distal tip with the proximal end of the cone section being used as a flange to engage body tissue such as the trabecular muscles inside the heart, with the smooth slope of the cone section minimizing trauma to the inside walls of blood vessels. (See U.S. Pat. No. 4,030,508 issued to Thalen on June 21, 1977). However, the anchoring effect of such devices is severely limited since the size of the flange is restricted by the inside diameter of the smallest vein through which the flange must pass.

There are prior art devices which employ flexible tines that extend from an electrode lead adjacent the distal tip and form an acute angle with the axis of the electrode lead. (See U.S. Pat. No. 3,902,501 issued to Citron et al. on Sept. 2, 1975). Flexible tines have also been extended from a ring which surrounds the electrode lead at a point behind the distal tip (See U.S. Pat. No. 4,033,357 issued to Helland et al. on July 5, 1977).

Provision has been made, for example in the above-mentioned Citron et al. patent, to hold tines against the electrode lead during insertion thereby reducing resistance to passage through veins. The tines are then released when the distal tip is in position. The primary disadvantage of such prior art arrangements comes from the abrupt transitions created at the base of the tines when they are in the folded configuration. Such abrupt transitions are a source of trauma to the inside walls of veins, cause increased resistance to passage of the electrode lead along the veins, and hence limit the minimum size vein through which such electrode leads may pass.

Still other prior art electrode leads employ retractable forward facing tines which are designed to be mechanically thrust into the wall of a muscle tissue and thereby hold a distal tip in place, at least for the first few days after insertion until tissue can grow around the electrode lead. (See U.S. Pat. Nos. 3,754,555 and 3,976,082 issued to Schmitt on Aug. 28, 1973 and Aug. 24, 1976 respectively). While this prior art approach has the advantage of not having any abrupt transitions present on the outside surface of the electrode lead during insertion, the mechanics required to project the tines after placement of the electrode lead are complex, costly, and subject to failure.

It is, accordingly, an object of the present invention to provide a simple electrode lead structure which minimizes resistance to insertion and yet effectively holds the distal tip of the electrode lead in position after insertion.

Additional objects and advantages of the invention will be set forth in part in the description which follows, and in part will be obvious from the description, or may be learned by practice of the invention. The objects and advantages of the invention may be realized and obtained by means of the instrumentalities and combinations particularly pointed out in the appended claims.

SUMMARY OF THE INVENTION

To achieve the foregoing objects, and in accordance with the purposes of the invention, as embodied and broadly described herein, the trailing tine electrode lead of the present invention comprises an exposed conductive distal tip and a conductive shank supporting the distal tip; an electrical conductor coupled to the proximal end of the shank; an insulating covering over the shank and conductor with the covering including a transitional section having a proximal end; and a plurality of flexible tines connected to the insulating covering at and trailing behind the proximal end of the transitional section for anchoring the electrode lead.

In a preferred embodiment the transitional section includes a truncated cone portion, with the cone portion having a minimum radius at its distal end and having the maximum radius at its proximal end. Preferably, the maximum radius of the transitional section approximately equals the radius of the insulating covering adjacent the proximal end of the transitional section plus the thickness of one of the tines to permit the tines to be folded substantially flat against the insulating covering behind the transitional section. While the insulating covering adjacent the proximal end of the transitional section may have a minimum outside radius which extends away from the distal tip at least the length of the tines, it is preferable that the insulating covering include means to facilitate selective removal of the electrode leads, for example, in the form of a truncated cone having a maximum radius located at the distal end of the cone.

The insulating covering may be a single piece of insulation which is integral with the tines or may comprise an insulating sheath over the conductor separate from the transitional section with the distal end of the sheath being overlapped by the proximal end of the transitional section. In the latter case, the tines may be physically connected either directly to the proximal end of the transitional section or directly to the sheath adjacent the proximal end of the transitional section.

The transitional section may have notches extending axially in the outside surface of the section which notches terminate at the proximal end of the section between the tines. The transitional section may also have one or more cylindrical portions. The flexible tines may extend away from the insulating covering in a plane parallel to the axis of the electrode lead and at an acute angle with the axis or may protrude helically from the proximal end of the transitional section.

DESCRIPTION OF THE DRAWINGS

A greater appreciation of the objects and advantages of the invention may be understood by a detailed description taken in conjunction with the drawings, wherein:

FIG. 1 illustrates a prior art electrode lead having flexible trailing tines;

FIG. 2 illustrates a prior art electrode lead having flexible trailing tines in a folded position;

FIG. 3 illustrates a trailing tined electrode lead in accordance with the teachings of the present invention;

FIG. 4 is a side view, partially cut away, of a preferred embodiment of the trailing tined electrode lead of the present invention;

FIG. 5 is a front view of the trailing tined electrode lead of FIG. 4;

FIG. 6 is a cross-sectioned side view of a preferred embodiment of the insulating coating of the trailing tined electrode lead of the present invention;

FIG. 7 is a side view is, partially cut away, of another embodiment of the insulating coating of the trailing tined electrode lead of the present invention;

FIG. 8 is a side view of another embodiment of the trailing tined electrode lead of the present invention;

FIG. 9 is a front view of the embodiment shown in FIG. 8;

FIG. 14b is a view of section A—A of FIG. 14a;

FIG. 14c is a view of section B—B of FIG. 14a;

DETAILED DESCRIPTION

Figure 10:
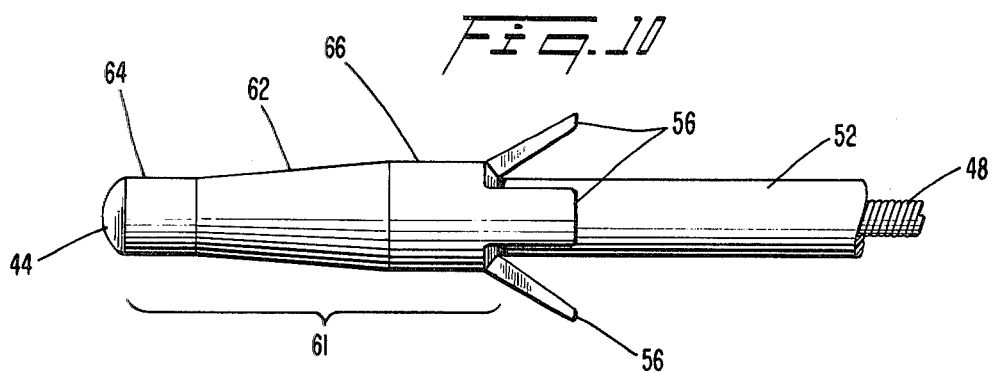
FIG. 10 is a side view of still another example of the insulating coating of the trailing tined electrode lead of the present invention.

Referring to FIG. 1, there is shown a prior art tined electrode lead having an exposed distal tip 10 and an electrical conductor 12 for electrically connecting a pulse of current from a pacemaker, not shown, at the proximal end of conductor 12 to distal top 10. For the purposes of the description and as used in the claims, "distal" refers to that end of the electrode lead or any part of the electrode lead nearest to the muscle to be stimulated and "proximal" refers to that end of the electrode lead or any part of the electrode lead nearest to the source of the pulses, such as a pacemaker. Distal tip 10 may contain a center insulating section, but must at least in part be conductive.

Electrical conductor 12 is typically a helically wound wire or plurality of interwound wires which is known in the art as a "helix" and which exhibits flexibility and strength. Distal tip 10 is typically supported by a conducting shank 14 which has an axial opening at its proximal end to receive the distal end of conductor 12.

Both conductor 12 and shank 14 are covered with an insulating coating 16. Coating 16 comprises a first section 18 of uniform outside diameter which insulates conductor 12. Coating 16 also comprises a second section 20 which insulates shank 14 and, accordingly, has a larger outside diameter than first section 18. Coating 16 preferably comprises silicone rubber or other flexible non-conductive material which is inert to body fluids.

A plurality of tines 22 are attached to coating 16 adjacent tip 10. The bases of tines 22 are fixed to second section 20 and tines 22 normally form an acute angle with the axis of shank 14 which angle opens away from distal tip 10. Tines 22, therefore, provide means for holding distal tip 10 in a desired position adjacent a muscle wall as a result of entrapment in trabeculae carnae.

Tines 22 are flexible and, hence, when tines 22 encounter an obstacle upon insertion of the electrode, such as the inside wall of a vein, tines 22 fold backward alongside second section 20 as shown in FIG. 2. It should be noted, however, that since tines 22 are attached to the outer surface of second section 20, tines 22 present an abrupt transition 24 to any obstacle encountered upon insertion of the electrode lead; e.g., a narrowing in the vein or small bore introduction catheter. It should also be noted that, when folded, the tines present a minimum cross-sectional width 26 which is as large as or greater than twice the cross-sectional width 28 of the tines plus the diameter 30 of second section 20. The effect of abrupt transition 24 and the magnitude of cross-sectional width 26 limit the utility of such prior art electrode leads for use in small openings, such as the small veins found in many patients.

Reference will now be made in detail to the present preferred embodiment of the invention which overcomes the abovementioned limitations of the prior art.

Referring to FIG. 3, there is shown an electrode lead 40 which generally illustrates the teachings of the present invention. Electrode lead 40 has an electrode tip assembly 42 which, as in the prior art of FIGS. 1 and 2, comprises an exposed distal tip 44 and a shank 46 supporting distal tip 44. An electrical conductor 48 has a distal end engaged within an axial opening at the proximal end of shank 46. As in the prior art, conductor 48 is preferably a helix and shank 46 may be swaged, crimped, or welded onto the distal end of conductor 48.

As was true with the prior art, the shank and conductor of the electrode are encased in an insulating means which is illustrated in FIG. 3 as insulation coating 50, with insulation coating 50 having a first section 52 of uniform outside diameter which forms an insulated sheath over conductor 48.

In accordance with the present invention, the insulating means for insulating the shank and conductor of the electrode includes a transitional section having a maximum radius at its proximal end and having means connected to the insulating means at, and trailing behind, the proximal end of the transitional section for anchoring the electrode lead. Preferably the means for anchoring comprise a plurality of flexible tines. By being attached to the proximal end of the transitional section, the tines do not present an abrupt transition to obstacles when folded and because the tines fold flat against the insulating means beyond the transitional section, the tines need not have a greater folded cross-sectional width than that presented by the proximal end of the gently tapering transitional section. Also, because the trailing tines in this invention fold flat against the conductor insulating means rather than against the larger-diameter shank insulation means as in the prior art, the trailing tines of this invention, when folded, can present a smaller cross-sectional width than could equivalent thickness tines of the prior art. Accordingly, the trailing tines electrode lead of the present invention facilitates insertion while maintaining the holding power of prior art tined electrodes.

Preferably, the transitional section of the insulating means includes a truncated cone portion with the cone having a minimum radius at the distal end and having the maximum radius of the transitional section at its proximal end. This minimum radius is preferably substantially equal to half the diameter of the distal tip, and the maximum radius is preferably substantially equal to the external radius of the insulating means beyond the transitional section plus the radial thickness of a folded tine.

As illustratively shown in FIG. 3, insulating coating 50 includes a second section 54 which, in the embodiment shown, comprises a truncated cone having a minimum radius at its distal end and a maximum radius at its proximal end. A plurality of flexible tines 56 are connected to insulating coating 50 at the proximal end of second section 54. Tines 56 are flexible and may be folded back along first section 52 of coating 50. Tines 56 normally, however, form an acute angle with the axis of conductor 48.

FIG. 4 is a side view, partially cut away, of a preferred embodiment of the trailing tined electrode lead of the present invention. Distal tip 44, shank 46, conductor 48, insulating coating 50, first section 52, second section 54, and tines 56 are all as described above with respect to FIG. 3.

In FIG. 4 first section 52 is shown to have a minimum outside radius which extends from the proximal end of second section 54 where tines 56 are located and extends away from distal tip 44 beyond the length of tines 56. Accordingly, with tines 56 attached to the proximal end of second section 54, the tines can be folded flat against coating 50 at first section 52 behind the proximal end of second section 54 to facilitate placement of distal tip 44. It is also important to note that when folded, tines 56 do not present any abrupt transition at point 58.

Preferably, with the insulation of first section 52 of minimum outside radius, the maximum radius at the proximal end of second section 54 is chosen substantially equal to that minimum radius plus the cross-sectional thickness of tines 56. Furthermore, the distal end of first section 52 may be overlapped by the proximal end of second section 54. In any event, it is preferable that the proximal end of second section 54 be located proximally beyond the proximal end of shank 46 to assure that tines 56 when folded lie against that portion of insulating coating 50 which has an outside diameter smaller than the maximum diameter of second section 54.

A frontal view of the electrode lead of the present invention is shown in FIG. 5. While four tines 56 are shown in FIG. 5, any suitable number may be employed, for example 3, 5, or 6. Tines 56 are preferably non-conductive and may be of any cross-sectional shape, although, the illustrated modified-rectangular shape is considered preferable.

As shown in FIG. 4, insulating coating 50 is preferably formed of two physically separate sections 52 and 54. However, sections 52 and 54 may form a single structure integral with tines 56 as shown in FIG. 6. Furthermore, although tines 56 are shown to be integral with second section 54 in FIG. 4, tines 56 may be physically connected to first section 52 adjacent the proximal end of second section 54 as shown in FIG. 7.

While the truncated cone portion of second section 54 is shown to have a continuous outside surface in FIG. 4, it is possible to practice the present invention as shown in FIGS. 8 and 9 with notches 60 extending axially in the outside surface of second section 54, which notches terminate at the proximal end of section 54 between tines 56.

Figure 13:
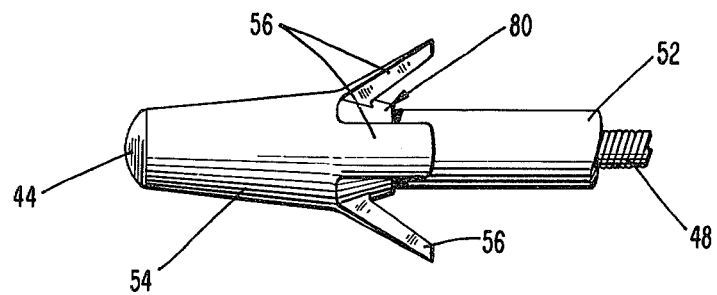
FIG. 13 is a side view of still another embodiment of the trailing tined electrode lead of the present invention.
Figure 14A:
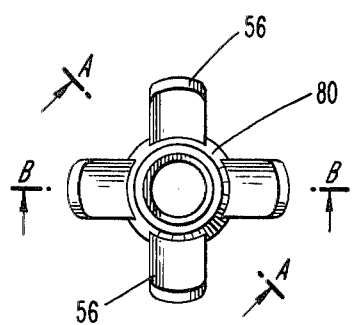
FIG. 14a is a top view of the embodiment of FIG. 13.
Figure 14B:
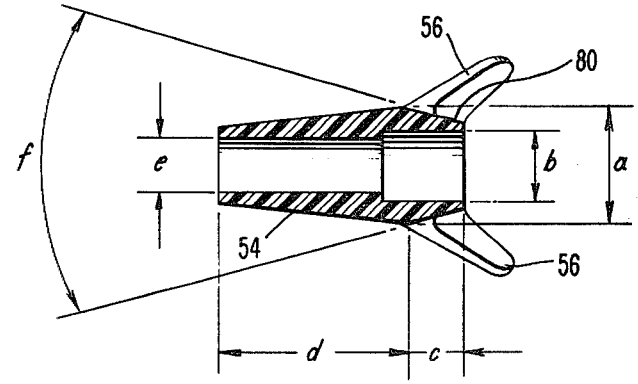
Figure 14C:
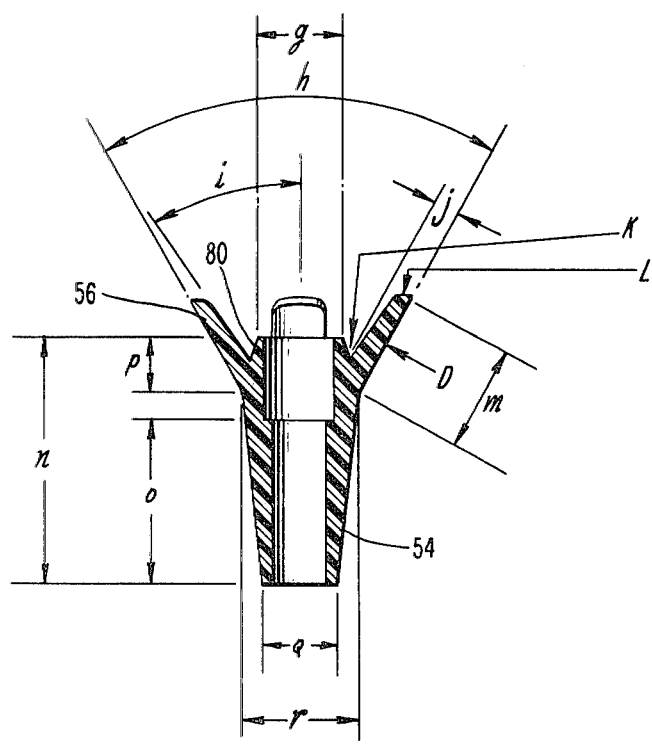
Figure 14D:
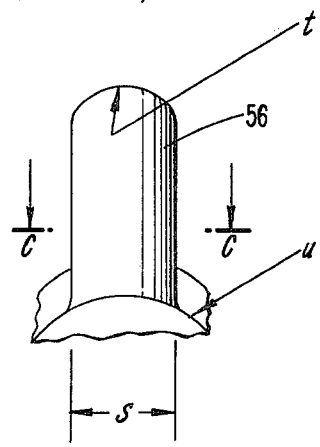
FIG. 14d is a part view of section D of FIG. 14c.
Figure 14E:
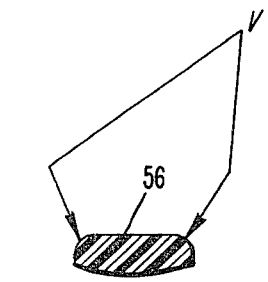
FIG. 14e is a view of section C—C of FIG. 14d.

It should also be understood that while FIG. 4 shows second section 54 to completely consist of a truncated cone, the second section may in fact comprise a truncated cone portion in combination with one or more cylindrical portions. For example, as shown in FIG. 10 a second section 61 comprises a cone portion 62 with a first cylindrical portion 64 interposed between distal tip 44 and the distal end of cone portion 62. A second cylindrical portion 66 is interposed between the proximal end of cone portion 62 and the proximal end of second section 61 where tines 56 are located. More than one cone portion may also be employed. Other geometric shapes approximating a transitional core could be used without departing from the spirit of this invention. For example, tines can trail behind a cylindrical section if distal tip diameter and diameter over folded tines are substantially equal. Also, one preferred embodiment has a subsidiary taper as the rear face of the transitional cone (see FIG. 13) forming a smooth transition between the diameters of sections 52 and 54.

Figure 11:
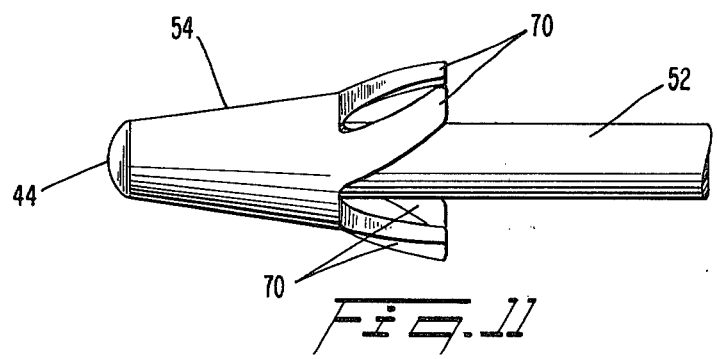
FIG. 11 is a side view showing helically trailing tines in accordance with the present invention.
Figure 12:
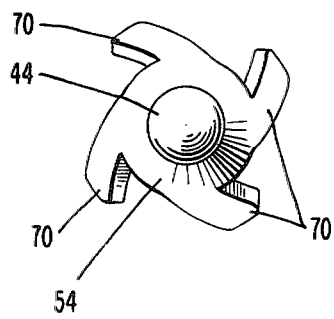
FIG. 12 is a front view of the embodiment of FIG. 11.

While tines 56 have been shown in FIG. 4 to extend axially beyond the proximal end of second section 54, the tines may extend helically beyond the proximal end of second section 54, as illustrated by tines 70 in FIGS. 11 and 12, to allow a screwing action when releasing the tines from trabeculae for repositioning.

The proximal end-face of the transitional cone may end abruptly in a plane perpendicular to the axis of the cone as discussed above. However, when removing the electrode lead from the heart, chordae tendinae tend to catch against the end-face of the transitional cone if it is ended abruptly. Substantial force is required to disengage such captured chordae tendinae which may bruise or break the chordae tendinae or cause other damage to the heart. To minimize the force required and thereby facilitate selective removal of the electrode lead while still maintaining the essential anchoring effect afforded by the trailing tines, a preferred embodiment of the present invention includes a second truncated cone portion located proximal to the transitional cone, with the second cone portion having a minimum radius at its proximal end substantially equal to the radius of the conductor insulating means 52, and having a maximum radius at its distal end substantially equal to and coincident with the radius of the proximal end of the transitional cone.

The axial length of the second cone portion should preferably be coincident with the axial length of the base of the tines, so that the additional material due to the addition of the second cone occurs substantially between the tines, not under the tines, thus allowing the folded tines to continue to lie substantially flat against the electrode lead, without presentation of any abrupt transition upon insertion of the lead.

FIGS. 13 and 14a–e illustrate an example of the present invention employing second truncated cone portion 80. The following provide suitable dimensions for the cone sections and tines made of heat vulcanizing silicone elastomer (medical grade by Dow Corning) shown in FIGS. 14a–e:

| Location | Size |
| --- | --- |
| a | 3.2 mm |
| b | 2.0 mm |
| c | 1.5 mm |
| d | 5.5 mm |
| e | 1.6 mm |
| f | 30° |
| g | 2.4 mm |
| h | 60° |
| i | 35° |
| j | 0.7 mm |
| k | R. 0.2 mm |
| l | R. 0.5 mm |
| m | 3.0 mm |
| n | 7.0 mm |
| o | 4.6 mm |
| p | 1.5 mm |
| q | 2.2 mm |
| r | 3.2 mm |
| s | 1.6 mm |
| t | Full Radius |
| u | R. 0.5 mm |
| v | R. 0.5 mm |

Although illustrated as unipolar ventricular endocardial leads, the present invention is applicable to endocardial heart stimulating electrode leads of the unipolar ventricular type, and bipolar ventricular type, the unipolar atrial type, the bipolar atrial type and the multipolar and multichamber types, or to any other applications where tines can enhance fixation of the distal tip and the lead must pass through a narrow bore constriction.

While a particular embodiment of the present invention has been shown and described, it will, of course, be obvious to one skilled in the art that certain advantages and modifications may be effected without departing from the spirit of the invention, and accordingly, it is intended that the scope of the invention not be determined by the foregoing examples but only by the scope of the appended claims.

What is claimed is:

1. A trailing tine electrode lead comprising:
   a. an exposed conductive distal tip and a conductive shank supporting said distal tip;
   b. an electrical conductor coupled to the proximal end of said shank;
   c. insulating means for insulating said shank and said conductor, said insulating means including a transitional section having a proximal end; and
   d. means connected to said insulating means at, and trailing behind, said proximal end of said transitional section for anchoring said electrode lead, said anchoring means comprising a plurality of foldable, flexible tines, said tines extending at an angle with respect to the longitudinal axis of said electrical conductor and when folded collapsing within the circumference of said transitional section.

2. The trailing tine electrode lead of claim 1 wherein said transitional section has a maximum radius at said proximal end.

3. The trailing tine electrode lead of claim 2 wherein said transitional section includes a truncated cone portion with said cone portion having a minimum radius at its distal end and having a maximum radius at its proximal end.

4. The trailing tine electrode lead of claim 3 wherein said maximum radius approximately equals the radius of said insulating means adjacent said proximal end of said transitional section plus the thickness of one of said tines.

5. The trailing tine electrode lead of claim 3 wherein said insulating means and said tines comprise a single integral piece of insulation.

6. The trailing tine electrode lead of claim 3 wherein said insulating means comprises an insulating sheath of uniform outside diameter covering said electrical conductor and wherein the distal end of said sheath is overlapped by the proximal end of said transitional section.

7. The trailing tine electrode lead of claim 6 wherein said tines are physically connected to the proximal end of said transitional section.

8. The trailing tine electrode lead of claim 6 wherein said tines are physically connected to said sheath adjacent the proximal end of said transitional section.

9. The trailing tine electrode lead of claim 3 wherein said transitional section has notches extending axially in the outside surface of said section which notches terminate at said proximal end of said section between said tines.

10. The trailing tine electrode lead of claim 3 wherein said transitional section includes at least one cylindrical portion.

11. The trailing tine electrode lead of claim 3 wherein said tines protrude helically from said proximal end of said section.

12. The trailing tine electrode lead of claim 3 wherein said insulating means adjacent said proximal end of said transitional section includes means for facilitating selective removal of said electrode lead.

13. The trailing tine electrode lead of claim 12 wherein said means for facilitating selective removal of said electrode lead includes a second truncated cone portion with said second cone portion having a maximum radius at its distal end and having a minimum radius at its proximal end.

14. A trailing tine electrode lead comprising:
   a. an exposed conductive distal tip and a conductive shank supporting said distal tips;
   b. an electrical conductor coupled to the proximal end of said shank;
   c. insulating means for insulating said shank and said conductor; and
   d. a plurality of flexible tines attached to said insulating means and extending from said insulating means at an acute angle with the axis of said conductor, said angle opening away from said electrode tip, wherein
      said insulating means includes a first section beginning at said tines and extending away from said distal tip and said insulating means includes a second section, at least a portion of which has the form of a truncated cone, said second section being located between said distal tip and said first section, the distal end of said second section having a first radius matching the radius of said distal tip, and the proximal end of said second section having a second radius matching the sum of the outside radius of said first section plus the thickness of one of said tines, and wherein said tines are attached to said insulating means at the transition between said first and second sections such that said tines may be folded proximally to lie flat against said first section, and such that when so folded, said tines present a maximum radius equal to and effectively continuous with said second radius of said second section.

15. A trailing tine electrode lead comprising:
a. an exposed conductive distal tip and a conductive shank supporting said distal tip;
b. an electrical conductor coupled to the proximal end of said shank;
c. insulating means for insulating said shank and said conductor; and
d. a plurality of flexible tines attached to said insulating means and extending from said insulating means at an acute angle with the axis of said conductor, said angle opening away from said electrode tip, wherein
said insulating means includes a first section beginning at said tines and extending away from said distal tip and said insulating means includes a second section, at least a portion of which has the form of a truncated cone, said second section being located between said distal tip and said first section, the distal end of said second section having a first radius matching the radius of said distal tip, and the proximal end of said second section having a second radius matching the sum of the outside radius of said first section plus the thickness of one of said tines, and wherein said tines are attached to said insulating means at the transition between said first and second sections such that said tines may be folded proximally to lie flat against said first section behind said second section.

16. The trailing tine electrode lead of claims 14 or 15 wherein said insulating means includes means to facilitate selection removal of said electrode lead.

17. The trailing tine electrode lead of claim 16 wherein said means to facilitate selective removal of said electrode lead includes a second truncated cone forming the transition between said first and second sections of said insulating means, said second truncated cone having a minimum radius at its proximal end matching the outer radius of said first section and having a maximum radius at its distal end matching said second radius at the proximal end of said second section.

18. The trailing tine electrode lead of claim 17 wherein said tines are attached to said insulating means at said second truncated cone.

19. The trailing tine electrode lead of claim 18 wherein the distal extremity of the base of said tines is coincident with the distal end of said second truncated cone, and wherein the proximal extremity of the base of said tines is coincident with the proximal end of said second truncated cone.

20. The trailing tine electrode lead of claims 1, 14, or 15 wherein said tines are non-conductive.

* * * * *